US009345768B2

(12) United States Patent
Jordan et al.

(10) Patent No.: US 9,345,768 B2
(45) Date of Patent: May 24, 2016

(54) NANOPARTICLE/ACTIVE INGREDIENT CONJUGATES

(75) Inventors: Andreas Jordan, Berlin (DE); Norbert Waldoefner, Berlin (DE); Klaus Decken, Berlin (DE); Regina Scholz, Berlin (DE)

(73) Assignee: MAGFORCE AG, Berlin (DE)

( * ) Notice: Subject to any disclaimer, the term of this patent is extended or adjusted under 35 U.S.C. 154(b) by 1042 days.

(21) Appl. No.: 11/911,196

(22) PCT Filed: Apr. 12, 2006

(86) PCT No.: PCT/DE2006/000653
§ 371 (c)(1),
(2), (4) Date: May 30, 2008

(87) PCT Pub. No.: WO2006/108405
PCT Pub. Date: Oct. 19, 2006

(65) Prior Publication Data
US 2008/0268061 A1   Oct. 30, 2008

Related U.S. Application Data

(60) Provisional application No. 60/675,100, filed on Apr. 27, 2005.

(30) Foreign Application Priority Data

Apr. 12, 2005  (DE) .................... 10 2005 016 873

(51) Int. Cl.
*A61K 9/14* (2006.01)
*A61K 31/407* (2006.01)
*A61K 31/70* (2006.01)
*A61K 33/24* (2006.01)
*A61K 38/00* (2006.01)
*A61K 39/395* (2006.01)
*A61K 35/04* (2006.01)
*A61K 41/00* (2006.01)
*A61K 9/00* (2006.01)
*A61K 9/16* (2006.01)
*A61K 47/48* (2006.01)
*B82Y 5/00* (2011.01)

(52) U.S. Cl.
CPC ........... *A61K 41/0052* (2013.01); *A61K 9/0009* (2013.01); *A61K 9/1676* (2013.01); *A61K 41/00* (2013.01); *A61K 47/48092* (2013.01); *A61K 47/48107* (2013.01); *A61K 47/48238* (2013.01); *A61K 47/48861* (2013.01); *A61K 47/48884* (2013.01); *B82Y 5/00* (2013.01)

(58) Field of Classification Search
None
See application file for complete search history.

(56) References Cited

U.S. PATENT DOCUMENTS

| 5,411,730 | A | 5/1995 | Kirpotin et al. ............... 424/322 |
| 6,147,205 | A * | 11/2000 | McGall et al. .................. 506/32 |
| 6,183,658 | B1 | 2/2001 | Lesniak et al. | |
| 6,767,635 | B1 | 7/2004 | Bahr et al. | |
| 7,530,940 | B2 * | 5/2009 | Hainfeld et al. .................. 600/1 |
| 2002/0141943 | A1 | 10/2002 | Kresse et al. | |
| 2003/0028071 | A1 | 2/2003 | Handy et al. | |
| 2005/0084539 | A1 | 4/2005 | Handa et al. | |

FOREIGN PATENT DOCUMENTS

| CA | 2476888 A1 | 8/2003 |
| CA | 2553647 A1 | 8/2005 |
| DE | 4428851 | 2/1996 |
| DE | 196 24 426 A1 | 1/1998 |
| DE | 10059151 | 6/2002 |
| EP | 0516252 | 12/1992 |
| JP | 2003-509034 A | 3/2003 |
| JP | 2004-305055 A | 11/2004 |
| KR | 10-2004-0092969 A | 4/2004 |
| WO | WO 97/38058 | 10/1997 |
| WO | WO 9858673 | 12/1998 |
| WO | WO 0243708 | 6/2002 |
| WO | WO 03026618 | 4/2003 |
| WO | WO-2004/096190 A1 | 11/2004 |
| WO | WO 2005042142 | 5/2005 |
| WO | WO 2005065282 | 7/2005 |
| WO | WO 2005070471 | 8/2005 |

OTHER PUBLICATIONS

Nasonova, et al. (1998) "Induction of Chromosomal Damage in CHO-K1 Cells and Their Repair-Deficient Mutant XRS5 by X-ray and Particle Irradiation", Advances in Space Research: The Official Journal of the Committee on Space Research (COSPAR), 22(4): 569-78 (Abstract Only).*
http://dictionary.reference.com/browse/adhesion (No Author, Volume Number, Issue Number, provided, (8 pages long).*
Raynal, et al. (2004) "Macrophage endocytosis of superparamagnetic iron oxide nanoparticles: mechanisms and comparison of ferumoxides and ferumoxtran-10", Investigative Radiology, 39(1): 56-63.*
Muro, et al. (2003) "Slow intracellular trafficking of catalase nanoparticles targeted to ICAM-1 protects endothelial cells from oxidative stress", American Journal of Physiology, Cell Physiology, 285(5); C1339-47.*
Derfus, et al. (2007) "Remotely Triggered Release from Magnetic Nanoparticles", Advanced Materials, 19: 3932-36.*

(Continued)

*Primary Examiner* — Robert M Kelly
(74) *Attorney, Agent, or Firm* — The Marbury Law Group, PLLC

(57) ABSTRACT

The present invention relates to nanoparticles, wherein at least one therapeutically active substance is bound to said nanoparticle and wherein the separation of the at least one therapeutically active substance from the nanoparticle is caused or initiated by an alternating magnetic filed. Furthermore, the present invention relates to pharmaceutical compositions, in particular to injection solutions containing the nanoparticles as well as to the use thereof for the treatment of cancer.

20 Claims, No Drawings

(56) References Cited

OTHER PUBLICATIONS

Nicewarner Pena, S. et al., "Hybridization and enzymatic extension of au nanoparticle-bound oligonucleotides"; J. Am. Chem. Soc. Jun. 26, 2002;124(25):7314-7323.

Kumar, C. et al., "Efficacy of lytic peptide-bound magnetite nanoparticles in destroying breast cancer cells"; J. Nanosci. Nanotechnol. 2004 4(3):245-249.

Examination Report in German Application No. DE 10 2005 016 873.6 dated Apr. 12, 2005.

Kennedy, Laura C. et al., "A New Era for Cancer Treatment: Gold-Nanoparticle-Mediated Thermal Therapies," Photothermal Therapy, Small, 2010, www.small-journal.com, pp. 1-15.

Xu, Y. et al., "Cobalt Nanoparticles Coated with Graphitic Shells as Localized Radio Frequency Absorbers for Cancer Therapy," Nanotechnology, Oct. 29, 2008, vol. 19, No. 43, 435102, Abstract only.

Zharov, V.P. et al., "Microbubbles-overlapping Mode for Laser Killing of Cancer Cells with Absorbing Nanoparticle Clusters," Journal of Physics D: Applied Physics, vol. 38, 2005, pp. 2571-2581.

* cited by examiner

NANOPARTICLE/ACTIVE INGREDIENT CONJUGATES

CROSS REFERENCE TO RELATED APPLICATIONS

This application is a national stage entry of international application no. PCT/DE2006/000653, of the same title, filed on Apr. 12, 2006, which claims priority to German application no. DE 10 2005 016 873.6, filed Apr. 12, 2005, and to U.S. Provisional Application No. 60/675,100, filed Apr. 27, 2005. The contents of the foregoing applications are incorporated herein by reference in their entireties.

The present invention relates to nanoparticles to which therapeutically active substances are bound, wherein the release of the therapeutically active substances is caused, initiated or substantially enhanced by an alternating magnetic field.

It is known that superparamagnetic nanoparticles can be used as excipients in the treatment of diseases. In this context, various approaches are followed. One known strategy is for example based on so called "magnetic drug targeting", in which attempts are made to realize a local increase in concentration of the active ingredients by means of a magnetic field (DE 10059151 A, Alexiou). Similarly, attempts are made to chemically convey target finding properties to the particles to realize an accumulation of said particles in certain body regions (DE 4428851 A1, EP 0516252 A2). Multishell particles for infiltrating tumor cells with conjugates consisting of the particle and of the active ingredient are described in the patent specification WO 98/58673 (INM).

The present invention aims at loading nanoparticles with therapeutically active substances such that no noteworthy release of the therapeutically active substances occurs in healthy tissue and such that a controlled release of the therapeutically active substance can take place once the nanoparticles have entered the tumor tissue and the tumor cells.

Said aim is achieved by the nanoparticles according to claim 1 as well as by the pharmaceutical composition according to claim 11 and by the use of said nanoparticles according to claim 12.

Further advantageous embodiments result from the dependent claims, the examples and the description.

The present invention relates to nanoparticles, wherein therapeutically active substances are bound to said nanoparticles and wherein the separation of the therapeutically active substances from the nanoparticles is caused, initiated or substantially enhanced by an alternating magnetic field. In this context, the at least one therapeutically active substance is released by means of the direct influence of the alternating magnetic field or due to the local heating caused by the alternating magnetic field. Preferably, the release is caused by the fact that a thermally labile linker between the active ingredient, i.e. the therapeutically active substance and the nanoparticle is thermally cleaved and/or that a linker is used which is labile with respect to an alternating magnetic field. Therefore, the present invention consists of binding a therapeutically active substance, in particular a cytostatic, to a nanoparticle by means of a linker which can be cleaved thermally and/or by a magnetic field.

The nanoparticles according to the invention are characterized in that at least one therapeutically active substance is bound to the nanoparticle and wherein the separation of the at least one therapeutically active substance from the nanoparticle is caused or initiated or substantially enhanced by an alternating magnetic field.

In other words, the present invention relates to nanoparticles, wherein at least one therapeutically active substance is covalently or ionically bound or bound via hydrogen bonds or via complexation (complex bond) or via intercalation or via lipophilic interactions by means of a linker and the linker can be cleaved due to thermal initiation or to initiation by an electromagnetic or respectively magnetic field.

Thermally initiated cleavage means that a local heating under physiological conditions to a temperature of more than 45° C., preferably more than 50° C. is sufficient to cleave the linker. Cleavage initiated by an electromagnetic or respectively magnetic field means that the application of an electromagnetic or respectively magnetic field under physiological conditions causes the linker to be cleaved, either only by the electromagnetic or respectively magnetic field and/or a local pH reduction induced by the electromagnetic or respectively magnetic field.

The at least one therapeutically active substance, i.e. the molecules of at least one therapeutically active substance class or one particular active ingredient is preferably bound by means of a covalent or predominantly covalent bond and/or a sufficiently strong ionic bond, clathrate compounds or complexation (complex bonds) or respectively by means of an arrangement of a sufficient number of hydrogen bonds or hydrophobic interactions so that an uncontrolled release of therapeutically active substance can substantially be avoided. Uncontrolled release describes the separation of therapeutically active substance in healthy tissue, particularly separation without an alternating magnetic field being active.

Such uncontrolled release results in therapeutically active substances being released at sites where they are more likely to cause detrimental side effects than therapeutic effects, that is outside of the carcinogenic tissue or respectively outside of the tumor cells.

Thus, the therapeutically active substances remain fixedly bound to the nanoparticles and are transported to the cancer cell together with the nanoparticle. While the nanoparticles are transported to the cancer cells, only minor up to insignificant amounts of the therapeutically active substances are released. Once arrived in the cancer cells, the therapeutically active substances are released by means of an alternating magnetic field, particularly by means of an exterior alternating magnetic field or respectively an alternating magnetic field applied from the outside (impulse).

In this context, "caused or initiated by an alternating magnetic field" means that the release or respectively separation is either directly caused by the alternating magnetic field or respectively the impulses or indirectly, for example by the activation or respectively induction of gene expression of enzymes or by the generation of heat.

The nanoparticles consist of a magnetic material, preferably a ferromagnetic, antiferromagnetic, ferrimagnetic, antiferrimagnetic or superparamagnetic material, further preferred of iron oxides, particularly of superparamagnetic iron oxides or of pure iron provided with an oxide layer. Such nanoparticles can be heated by an alternating magnetic field. The tissue containing the nanoparticles can be heated to a temperature of more than 50° C. Such high temperatures can be achieved due to the fact that up to 800 pg and more of iron in form of the nanoparticles can be absorbed per tumor cell.

Preferably, the nanoparticles consist of iron oxides and particularly of magnetite ($Fe_3O_4$), maghemite ($\gamma$-$Fe_2O_3$) or mixtures of said two oxides. In general, the preferred nanoparticles are represented by the formula $FeO_X$, wherein X is a number from 1 to 2. Preferably, the nanoparticles have a diameter of less than 500 nm. Preferably, the nanoparticles have an average diameter of 15 nm or are within the range of 1-100 nm and particularly preferred within the range of 10-20 nm.

In addition to the magnetic materials of the formula $FeO_X$, wherein X is a number within the range from 1.0 to 2.0, materials of the general formula $MFe_2O_4$ with M=Co, Ni, Mn, Zn, Cd, Ba or other ferrites can be used according to the invention. Furthermore, silica or polymer particles, into which magnetic materials, such as the magnetic materials mentioned herein are incorporate and/or to which such materials are bound are also suitable.

Therapeutically active substances are bound to said nanoparticles, in particular to superparamagnetic nanoparticles, wherein a covalent bond is preferred. Therapeutically active substances that may be selected include antiproliferative, anti-migration, antiangiogenic, antithrombotic, anti-inflammatory, antiphlogistic, cytostatic, cytotoxic, anticoagulative, antibacterial, antiviral and/or antimycotic agents, wherein antiproliferative, anti-migration, antiangiogenic, cytostatic and/or cytotoxic substances as well as nucleic acids, amino acids, peptides, proteins, carbohydrates, lipids, glycoproteins, glycans or lipoproteins having antiproliferative, anti-migration, antiangiogenic, antithrombotic, anti-inflammatory, antiphlogistic, cytostatic, cytotoxic, anticoagulative, antibacterial, antiviral and/or antimycotic properties are preferred. Furthermore, such substances may also be radiosensitizers or sensitizers or amplifiers of other combined conventional cancer treatment methods or contain such sensitizers.

As cytotoxic and/or cytostatic compounds, i.e. chemical compounds having cytotoxic and/or cytostatic properties the following may be used: alkylating agents, antibiotics having cytostatic properties, antimetabolites, microtubule inhibitors and topoisomerase inhibitors, compounds containing platinum and other cytostatics such as for example, asparaginase, tretinoin, alkaloids, podophyllotoxins, taxanes and Miltefosine®, hormones, immunomodulators, monoclonal antibodies, signal transductors (molecules for signal transduction) and cytokines.

Examples for alkylating agents include among others: chlorethamine, cyclophosphamide, trofosfamide, ifosfamide, melphalan, chlorambucil, busulfan, thiotepa, carmustine, lomustine, dacarbazine, procarbazine, temozolomide, treosulfan, estramustine and nimustine.

Examples for antibiotics having cytostatic properties include daunorubicin, doxorubicin (adriamycin), dactinomycin, mitomycin C, bleomycin, epirubicin (4-epi-adriamycin), idarubicin, mitoxantrone, amsacrine and actinomycin D.

Methotrexate, 5-fluorouracil, 6-thioguanin, 6-mercaptopurine, fludarabine, cladribine, pentostatin, gemcitabine, cytarabine, azathioprine, raltitrexed, capecitabine, cytosine arabinoside, thioguanine and mercaptopurine can be mentioned as examples for antimetabolites (antimetabolic agents).

Vincristine, vinblastine, vindesine, etoposide as well as teniposide are counted among the class of alkaloids and podophyllotoxins. In addition, compounds containing platinum can be used according to the invention. Cisplatin, carboplatin and oxaliplatin are examples for compounds containing platinum. Among the microtubule inhibitors are counted for example alkaloids such as vinca alkaloids (vincristine, vinblastine, vindesine, vinorelbine) and paclitaxel (Taxol®) as well as derivatives of paclitaxel. Examples for topoisomerase inhibitors include etoposide, teniposide, camptothecin, topotecan and irinotecan.

Paclitaxel and docetaxel are examples for the compound class of taxanes and among the other cytostatic substances (other cytostatics) are counted for example hydroxycarbamide (hydroxyurea), imatinib, Miltefosine®, amsacrine, topotecan (inhibitor of topoisomerase-I), pentostatin, bexarotene, biolimus A9, rapamycin (sirolimus), rhodomycin D, amethantrone, bendamustine, oxazaphosphorine, 5'-deoxy-5-fluorouridine, 9-aminocamptothecin, podophyllotoxin derivatives, mitopodozide, vinca alkaloids, calicheamicins, maytansinoids, tretinoin and asparaginase. Representatives of the compound class of monoclonal antibodies are among others trastuzumab (also known as Herceptin®), alemtuzumab (also known as MabCampath®) and rituximab (also known as MabThera®).

According to the invention, hormones such as for example glucocorticoids (prednisone), estrogens (fosfestrol, estramustine), LHRH (buserelin, goserelin, leuprorelin, triptorelin), flutamide, cyproterone acetate, tamoxifen, toremifen, aminoglutethimide, formestane, exemestane, letrozole and anastrozole can also be used. Among the classes of immunomodulators, cytokines, antibodies and signal transductors are counted interleukin-2, interferon-α, erythropoietin, G-CSF, trastuzumab (Herceptin®), rituximab (MabThera®), gefitinib (Iressa®), ibritumomab (Zevalin®), levamisole as well as retinoids.

Preferably, the aforementioned substances are covalently bound to the nanoparticles. The substances may for example be bound via hydroxy groups, amino groups, carbonyl groups, thiole groups or carboxyl groups, depending on the functional groups the respective substance is carrying. Thus, doxorubicin may for example be bound via its primary hydroxy groups in form of an ester; platinum derivatives (cisplatin, carboplatin, oxaliplatin, etc.) can be coupled to an amino group by means of nucleophilic substitution at the platinum; or paclitaxel can be bound via an imine bond.

Hydroxy groups are preferably bound as ester, acetal or ketal; thio groups are preferably bound as thioester, thioacetal or thioketal; amino groups are preferably bound as amides and partially also as imines (Schiff bases) or as urethane by reacting with an isocyanate group; carboxyl groups are preferably bound as esters or amides and carbonyl groups are preferably bound as acetals or respectively ketals.

The preparation of nanoparticles without active ingredient and without coating is described in detail in DE 4428851 A. Furthermore, functionalization of the surface of the nanoparticles is known, so that amino groups, hydroxy groups, carboxyl groups or carbonyl groups can be generated on the surface of the nanoparticles using known procedures.

Therefore, the present invention relates to nanoparticles having a plurality of amino groups, hydroxy groups, carboxyl groups or carbonyl groups on their surfaces and wherein linkers are bound to at least one part of said functional groups by means of an imine bond, amine bond, ester bond, amide bond or ketal bond and furthermore said linkers bind the therapeutically active substance in a covalent, ionic, complexed, lipophilic way or by means of hydrogen bonds.

A particular feature of a preferred embodiment of the inventive nanoparticles consists in the active ingredients being coupled to the magnetic nanoparticles by means of special types of bonds. Said bonds are constructed such that a release of the active ingredients can be stimulated by means of an exterior alternating magnetic field (impulse).

An alternating magnetic field acts as external stimulus which in the case of superparamagnetic particles triggers various relaxation processes of the particles. Among others, said processes result in a heating of the particles and their surroundings. According to the invention, said processes triggered by the alternating magnetic field are used to cleave the bond between nanoparticle and therapeutically active substance or to strongly accelerate the cleaving process. In this context, the rate of cleavage by biological processes (e.g. enzymatic cleavage) may be strongly enhanced by the impulse, so that the increase in concentration of the active ingredient at the destination may only be achieved once the impulse has been applied. Similarly, the bond can be constructed such that a cleavage by chemical reactions (e.g. hydrolysis) is triggered or significantly accelerated. Furthermore, the heating induced by the magnetic field may cause a nucleic acid molecule or a polypeptide molecule used as a linker to melt.

The therapeutically active substances are bond directly or via a linker molecule. The linker molecule is preferably bound to the nanoparticles or to the respective nanoparticle by means of an amide bond or ester bond.

According to the invention, it is also possible that nucleic acids (deoxyribonucleic acids (DNA), ribonucleic acid (RNA) or peptide nucleic acids (PNA)) or polypeptides of various lengths can be used as linkers. The necessary molecules can optionally be produced either genetically or synthetically. The linkers may be cleaved in a thermally induced, magnetically induced or acid induced way under physiological conditions. Cleavage of the linker means that the linker contains at least one bond within the linker which bond can be cleaved under physiological conditions due to the impact of heat, the influence of a magnetic field, i.e. of a magnetic impulse or due to an exposure to acid. Due to the exposure to heat (preferably at least 45° C.) and/or to the magnetic field and/or to acid said bond should be cleaved at least twice as rapidly under physiological conditions as it is the case if such exposure is not provided. The formation of acid and the reduction of the local pH may for example be caused by already killed cells. The expression "bond within the linker" also comprises the bond of the linker to the nanoparticle as well as the bond of the linker to the therapeutically active substance. Besides, the linker may also be composed of two or three linker molecules.

In order to guarantee for the cleavability required, the linkers have at least one of the following functional groups: —S—S—, —O—P(=O)(O⁻)—O—, —CO—CO—, —NH—CO—CO—NH—, —C=N—C, ketals, —CO—NH—N=C—, trioxy silanes (—O—)(—O—)(—O—) Si—C or acetals.

For example, suitable linkers may have the following form:

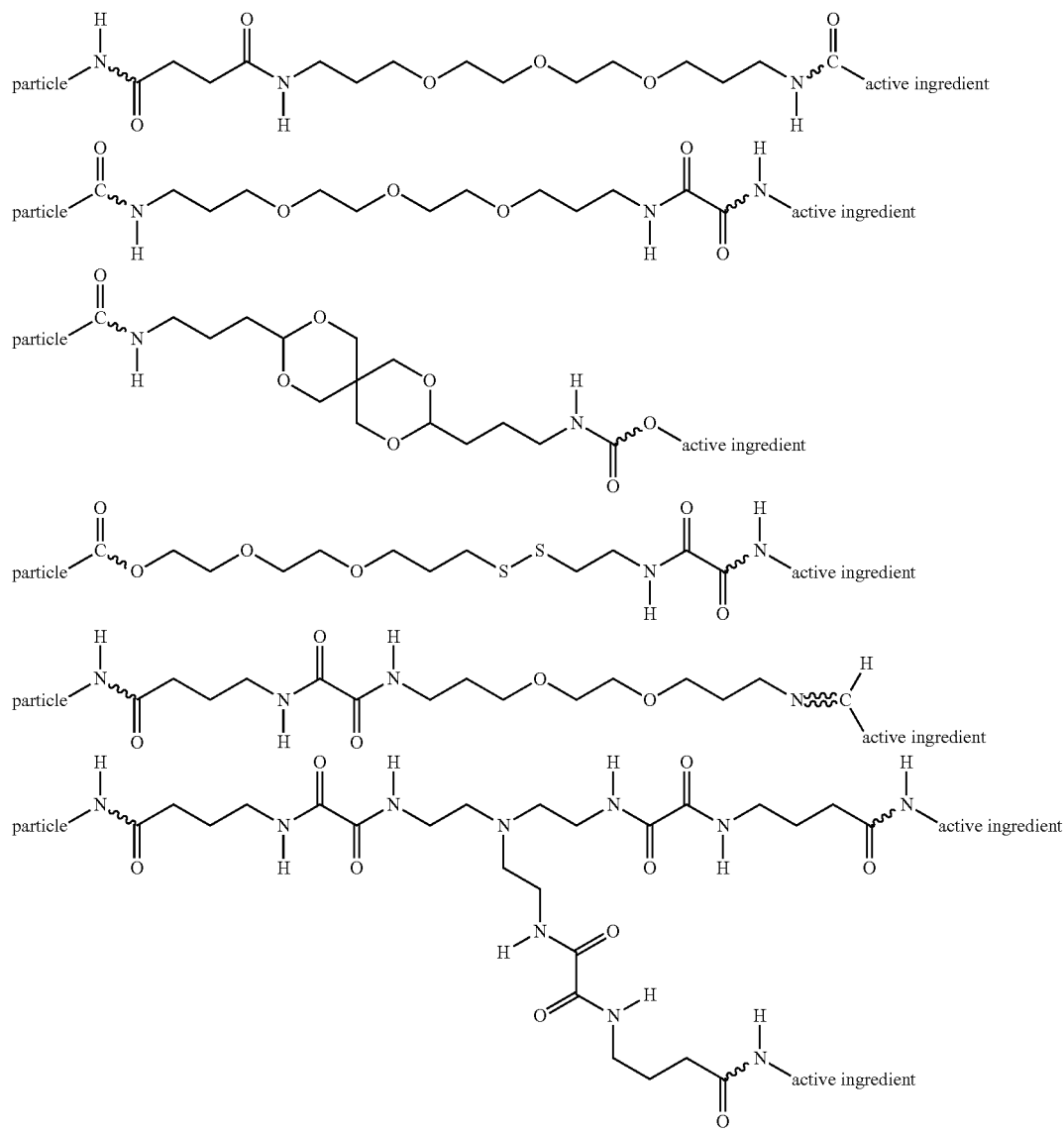

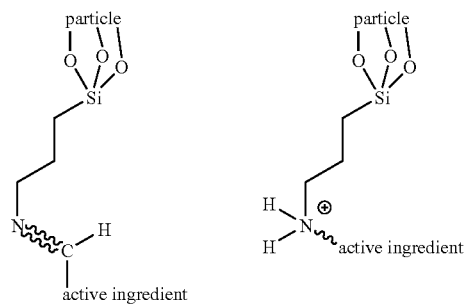 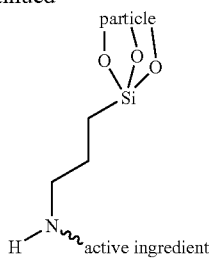

The zigzag line indicates the bond between active ingredient and the linker or respectively between the linker and the nanoparticle.

Preferred nucleic acids are such constructs, preferably double stranded constructs, having a fusion point within in the range of 40 to 60° C. When double stranded DNA, RNA or PNA is used, a strand disposes of a group capable of coupling to the particle (e.g. an amino or carboxy group coupled via a phosphoramidate group). The complementary strand may for example carry the active ingredient which is also coupled via a covalent bond. Due to the base pairing between the strands, the active ingredient is also coupled to the particles. The active ingredient can only be released when the double helix is melted open due to the generation of heat in the alternating magnetic field. In this process, the single strands are separated and the active substance is decoupled from the particle. Both the melting point and the degradation of the linker can be controlled by selecting corresponding homo hybrids or hetero hybrids from DNA-DNA, DNA-RNA, DNA-PNA, RNA-RNA, RNA-PNA or PNA-PNA.

Preferred polypeptides are such molecules which tend to form defined homo dimers or hetero dimers, particularly via hydrogen bonds (such as e.g. between immunoglobulin domains) or via hydrophobic interactions (such as e.g. in the so called leucine zippers). In said cases too, such pairs having a melting point within the range of 40 to 60° C. and which therefore are predominantly present in paired state under physiological conditions but which do not disintegrate into their monomers at therapeutically achievable temperatures are used. For said purpose, one binding partner is covalently coupled to the nanoparticle and the other is covalently coupled to a therapeutically active substance. When the bond between the two peptide strands is melted nanoparticles are decoupled and therapeutically active substances which afterwards, possibly only subsequent to cleavage such as enzymatic cleavage, are present in freely diffusible form.

Similarly, interactions between polypeptide and nucleic acid can be used in a corresponding linker. For said purpose, polypeptides interacting in a non-covalent manner with nucleic acids and capable of binding nucleic acids are coupled to the nanoparticles. Said interactions can also be melted by the impact of heat, so that the bound nucleic acid is released in addition to the coupled effector molecule. Sometimes even the released nucleic acid itself can act as an effector molecule (for example siRNA, antisense DNA, etc.). Potential polypeptides binding nucleic acids are in particular zinc fingers having a length of between 20 and 50 amino acids, but also the frequent helix-turn-helix motif of DNA-binding domains can be used or the "single stranded binding protein" (SSB) for DNA binding (a small protein having a DNA binding domain of about 100 amino acids) or respectively the "RNA recognition motif" (RRM or respectively RNP-1) of single stranded RNA binding proteins (measuring about 90 amino acids) or the "double stranded RNA binding motif" (DRBM) of double stranded RNA binding proteins (measuring about 65 amino acids).

Another variation consists in using the bond of low molecular weight ligands by nucleic acids (aptamers) or respectively proteins in a linker system. Generally, all molecules can be used, for example by producing antibodies against such a so called "haptene" (for example antibodies against dinitrophenol, trinitrophenol, digoxigenine, digoxin, biotin are frequently used). In particular binding pockets of biomolecules, such as for coenzymes (such as coenzyme A, ATP, GTP, FAD, NADH, NADPH, biotin, folic acid, pyridoxal phosphate, etc.), substrates (such as the glutathione binding site of glutathione-S-transferase GST comprising 73 amino acids) or hormones (such as the hormone binding domain of the nuclear hormone receptors for androgens, estrogens, retinoic acid, thyroxine, vitamin D3 measuring from 218 to 252 amino acids) are also practicable. One of the most frequently used interactions and simultaneously the strongest known non-covalent bond is that of biotin to avidin or respectively streptavidin. Due to the high binding avidity, it may be better to use modified avidin or respectively biotin analogues (for example desthiobiotin or iminobiotin) with a less strong bond, in order to realize melting within a range of temperatures that can be technically achieved. In all cases, it makes sense to couple the micromolecular ligand to the effector molecule and to couple the macromolecular ligand to the nanoparticles; however, depending on the choice of ligand, the inverse arrangement may also be advantageous.

In this preferred embodiment, the only coupling methods considered are methods generating a bond between the nanoparticle and the active ingredient, wherein said bond is sufficiently stable under "normal" physiological conditions, but considerably less stable under the conditions (impulse) used according to the invention. The mechanism of release per se and thus also the type of bond depend on the target (e.g. tumor in the case of cancers) and have to be adjustable by means of conventional chemical coupling methods. Similarly, the release can occur intracellularly (e.g. in tumor cells) or extracellularly. The particles produced according to the invention differ from known carriers of active ingredients in that efficiency can only be achieved by activation in the alternating magnetic field, while without said impulse the active ingredient remains largely ineffective.

According to the invention the nanoparticle/active ingredient conjugates are preferably based on magnetic cores containing iron; said cores are surrounded by one or more colloidal sheaths or coatings which allow for the active ingredients to be coupled thereto via functional groups. The core preferably consists of magnetite or maghemite. The primary function of the sheaths consists of realizing a colloidal distribution in the aqueous medium and of protecting the nanoparticles from agglomerations. In principle, particles with several sheaths as described in WO 98/58673 are a suitable basis for nanoparticle/active ingredient conjugates which can be activated, since the biological behavior of such particles can be adjusted by means of coatings with polymers and since the active ingredients may be coupled to functional groups of the primary sheath.

The active ingredients can be coupled to the primary sheaths using different methods. In the event that the particle cores are stabilized by amino silanes or by a sheath or respectively coating carrying an amino group the active ingredients may for example be coupled to an amino group situated close to the surface. In this context, the coupling may be carried out via e.g. succinimidyl esters, sulfosuccinimidyl esters, isothiocyanates, triazinyl chlorides, sulfonyl chlorides, tetrafluorophenyl esters or also via aldehyde groups. For this purpose, the active ingredient has to be capable of being coupled with such groups by a chemical method. If the active ingredient cannot be coupled directly using said methods, a linker molecule may be employed. Said "linker" connects the active ingredient with the functional groups of the protective sheath and thus improves the variability regarding the different coupling possibilities. Therefore, it is preferred that the linker molecule contains a group which is thermolabile, electromagnetically labile, photolabile, acid-labile, intercalated or may be intercalated or cleaved by enzymatic cleavage. Furthermore, the release mechanism can also be controlled via the linker. Thus, the linker can also introduce groups which allow for the active ingredients to be cleaved. Potential groups include for example cleavable acetal, ester, hydrazone or imine groups. Similarly, peptide sequences are suitable for the use as such linkers in which the active ingredient is only released after an enzymatic cleavage or subsequent to melting of a non-covalent bond. Furthermore, DNA, RNA and PNA molecules may be used as, preferably, double stranded linkers, wherein the release occurs by thermally induced melting of the double strands.

According to the invention, only such linkers may be used which do not cause any or only slow cleavage rates under normal physiological conditions. The linker molecules can for example be constructed such that, even though a release in the target region (e.g. enzymatic release in the tumor cell) is possible, said release is so slow under normal conditions that it is impossible to achieve a therapeutic concentration of the active ingredient. Cleavage of the linker molecule or respectively cleavage of the linker molecule at sufficiently high speed is only caused as a consequence of the impulse from the outside by the alternating magnetic field and results in the activation of the active ingredient. Preferably, this aim is realized by the fact that such conformation permitting enzymatic cleavage of the linkers is only achieved once a thermally induced melting of nucleic acid double strands or respectively multiple strands or alternatively of peptide dimers or respectively peptide oligomers has taken place.

Particles stabilized by various functional groups (e.g. carboxy, epoxy, aldehyde) can be treated in the same way as particles stabilized by amino silane. It is critical that the coupling method is selected such that a release can only take place under the conditions mentioned above. Similarly, an active ingredient can be coupled to an alkoxy silane that has been functionalized with the abovementioned groups (see example 1), wherein in a subsequent step said conjugate is coupled to the protective sheath of particles that have already been stabilized by silanes. The coupling is not limited to covalent bonds. According to the invention it is also possible to generate ionic interactions having sufficient stability.

Further coating of the nanoparticle/active ingredient conjugates which can be activated (e.g. with polymers) as described in patent specification no. WO 98/58673 is also possible and may be used for improving the biological characteristics of the particle/active ingredient conjugates. Similarly, other molecules conveying target finding properties to the complete construct may be coupled (e.g. polyclonal antibodies, monoclonal antibodies, humanized antibodies, human antibodies, chimeric antibodies, recombinant antibodies, bispecific antibodies, antibody fragments, aptamers, Fab fragments, Fc fragments, peptides, peptidomimetics, gap-mers, ribozymes, CpG oligomers, DNA-zymes, riboswitches or lipids. To realize this aim, the further modifications must not interfere with the release (which may be activated) of the active ingredient at the target.

Thus, various molecules having up to 500 carbon atoms or 10 to 30 base pairs, preferably 15-25 base pairs or 10-30 amino acids, preferably 15 to 25 amino acids may serve as linkers, provided that the linker contains a group which can be thermally, photochemically or enzymatically cleaved, an acid-labile group or any other group that can be easily detached. Therefore, a bond within the linker molecule and/or the bond of the linker to the active ingredient and/or the bond of the linker to the surface of the nanoparticle have to be either directly cleavable by the action of the alternating magnetic field or indirectly cleavable. Indirect cleavage means that enzymes such as peptidases, esterases or hydrolases are excited at the target, e.g. in the cancer cell, for example by means of the alternating magnetic field or that their activity or expression is enhanced and said enzymes are capable of performing the aforementioned cleavage. Besides, indirect cleavage may occur when magnetic nanoparticles are used, if said particles are heated by the alternating magnetic field, leading to the cleavage of a thermally labile bond. Also, the increase of the pH at the target by the action of the alternating magnetic field and the subsequent cleavage of acid-labile bonds within the linker molecule is to be contemplated.

The ester group and the amide or respectively peptide group are part of the enzymatically cleavable groups within or at the linker molecule. Groups that can be cleaved thermally or by means of an acid comprise e.g. phosphate groups, thiophosphate groups, sulfate groups, phosphamide groups, carbamate groups or imine groups.

The active ingredient does not necessarily have to be bound covalently to the linker; instead, it can also be bound ionically or via hydrogen bonds or may be present in an intercalated or complexed form.

Furthermore, it is also possible to adsorptively bind the active ingredients to the surface of the nanoparticles and to cover them with a barrier layer that, to a large extent, prevents the release of the active ingredient until the barrier layer has been modified, in particularly disintegrated, by the action of an alternating magnetic field such that the active ingredient may be released.

In other preferred embodiments the inventive nanoparticles are surrounded or respectively covered by one or more sheaths or coatings. Said sheaths or coatings may have one or more functions and may serve as protective sheath, barrier layer or cell-selective coating.

In the event that the bond of the therapeutically active substances to the nanoparticles is weak, for example in the case of a non-covalent, ionic, adsorptive, lipophilic and/or van der Waals bond and/or an attachment by means of hydrogen bonds, a protective sheath or barrier coating can prevent the release of the therapeutically active substances until the nanoparticles have reached their destination. An exterior layer carrying cell-specific functionalities may be applied to the protective sheath or barrier coating instead of said protective sheath or barrier coating or as a further layer on this protective sheath or barrier coating.

Said cell-specific coating increases the affinity of the nanoparticles for certain cells, for example for certain bacterial cells or for certain tumor cells; consequently, it serves for cell discrimination. Such cell-specific nanoparticles preferably accumulate in cells, for which their affinity is increased due to the functionality on their surface; consequently such nanoparticles are tumor specific. Thanks to this technology, tumor specific nanoparticles, for example for certain types of cancer may be developed.

Furthermore, the nanoparticles may also be stabilized by a colloidal protective sheath preventing the nanoparticles from agglomerating. Preferably, such protective sheaths or coatings are provided with amino groups or carboxy groups. Biological, synthetic or semisynthetic polymers may be used for the protective sheathings or respectively coatings. Polymers, preferably biostabile polymers, i.e. polymers that are largely resistant to biological degradation are typically used for generating a barrier layer. For the generation of cell specific-sheaths or respectively coatings, it is preferred to use biodegradable polymers.

The following polymers may be used as biostable polymers: polyacrylic acid and polyacrylates such as polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halides, polyvinylidene halides, polyvinyl ethers, polyisobutylenes, polyvinyl aromatics, polyvinyl esters, polyvinyl pyrrolidones, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, EPDM rubbers, fluorosilicones, carboxymethyl chitosans, polyaryletheretherketones, polyetheretherketones, polyethylene terephthalate, polyvalerates, carboxymethyl cellulose, cellulose, rayon, rayon triacetate, cellulose nitrates, cellulose acetates, hydroxyethyl cellulose, cellulose butyrates, cellulose acetate butyrates, ethyl vinyl acetate copolymers, polysulfones, epoxy resins, ABS resins, silicones such as polysiloxanes, polydimethylsiloxanes, polyvinyl halogens and copolymers, cellulose ethers, cellulose triacetates, chitosans and copolymers and/or mixtures of said substances.

The following polymers may be used as biodegradable polymers: polyvalerolactones, poly-ε-decalactones, polylactonic acid, polyglycolic acid, polylactides, polyglycolides, copolymers of polylactides and polyglycolides, poly-ε-caprolactone, polyhydroxy butyric acid, polyhydroxybutyrates, polyhydroxyvalerates, polyhydroxybutyrate-co-valerates, poly(1,4-dioxane-2,3-diones), poly(1,3-dioxane-2-ones), poly-para-dioxanones, polyanhydrides such as polymaleic acid anhydrides, polyhydroxymethacrylates, fibrin, polycyanoacrylates, polycaprolactone dimethylacrylates, poly-β-maleic acid, polycaprolactone butyl acrylates, multiblock polymers such as e.g. from oligocaprolactone diols and oligodioxanone diols, polyether ester multiblock polymers such as e.g. PEG and poly(butylene terephthalate), polypivotolactones, polyglycolic acid trimethyl carbonates, polycaprolactone glycolides, poly(γ-ethyl glutamate), poly(DTH-iminocarbonate), poly(DTE-co-DT-carbonate), poly(bisphenol A iminocarbonate), polyorthoester, polytrimethyl carbonates, polyiminocarbonates, poly(N-vinyl)-pyrrolidone, polyvinyl alcohols, polyester amides, glycolized polyesters, polyphosphoesters, polyphosphazenes, poly[(p-carboxyphenoxy)propane], polyhydroxy pentanoic acid, polyanhydrides, polyethylene oxide propylene oxide, soft polyurethanes, polyurethanes having amino acid residues in the backbone, polyether esters such as polyethylene oxide, polyalkene oxalates, polyorthoesters as well as copolymers thereof, lipids, carrageenans, fibrinogen, starch, collagen, protein based polymers, polyamino acids, synthetic polyamino acids, zein, modified zein, polyhydroxyalkanoates, pectic acid, actic acid, modified and unmodified fibrin and casein, carboxymethyl sulfate, albumin, hyaluronic acid, chitosan and derivatives thereof, heparan sulfates and derivates thereof, heparins, chondroitin sulfate, dextran, β-cyclodextrines, alginates, glycosaminoglycans, saccharides, polysaccharides, proteoglycans, glycoproteins, copolymers with PEG and polypropylene glycol, gum arabic, guar, gelatin, collagen N-hydroxysuccinimide, phospholipids, modifications and copolymers and/or mixtures of the aforementioned substances.

In order to further increase affinity with respect to certain cells, monoclonal antibodies and/or aptamers can be coupled onto the surface of the nanoparticles or respectively onto the exterior layer or sheath of the nanoparticles. The monoclonal antibodies and aptamers are designed such that they are capable of recognizing certain cells, such as tumor cells, and further enhance cell discrimination of the nanoparticles.

In a preferred embodiment of the present invention, the cores of the magnetic nanoparticles consist of magnetite ($Fe_3O_4$), maghemite ($\gamma$-$Fe_2O_3$) or of mixtures of said two oxides and preferably they are superparamagnetic. Additionally, the cores are stabilized by colloidal protective sheaths, allowing for an attachment of the therapeutically active substances. Due to the type of bond, the conjugates of magnetic nanoparticles and therapeutically active substances are constructed such that controlled release of the therapeutically active substance in the human body can be caused by means of an alternating magnetic field (impulse).

Furthermore, the present invention relates to pharmaceutical compositions containing the inventive nanoparticles as well as to the use of the inventive nanoparticles for preparing such pharmaceutical compositions.

In particular, said pharmaceutical compositions are infusion or injection solutions. Such solutions of the nanoparticles, for example in physiological saline, are suitable for interstitial or respectively intratumoral administration. Intraarterial or intravenous administration further allows for a systemic therapy regarding the whole body, in the case of non-solid tumors and/or kinds of tumors that form metastases.

The nanoparticles and pharmaceutical compositions according to the invention are used both for treatment and prophylaxis of diseases characterized by degenerated cell species or foreign cells and in which the characteristics of the inventive nanoparticles consisting in the fact that they are capable of discriminating between foreign cells or respectively degenerated cells and healthy autologous cells can be advantageously used. Among the degenerated cells are particularly counted cancer cells or respectively cells that are defective regarding their proliferation and stenotic or restenotic tissue. Foreign cells include in particular bacterial cells.

Accordingly, the inventive nanoparticles and the pharmaceutical compositions containing the nanoparticles are used for prophylaxis and treatment of tumors, carcinomas and cancer.

Examples for types of cancers and tumors, for which the inventive nanoparticles can be used include the following: adenocarcinomas, choroidal melanoma, acute leukemia, acoustic neurinoma, ampullary carcinoma, anal carcinoma, astrocytomas, basal cell carcinoma, pancreatic cancer, connective tissue tumor, bladder cancer, bronchial carcinoma, non-small cell bronchial carcinoma, breast cancer, Burkitt's lymphoma, corpus carcinoma, CUP syndrome, cancer of the large intestine, cancer of the small intestine, tumors of the small intestine, ovarian cancer, endometrial carcinoma, ependymoma, epithelial cancers, Ewing tumors, gastrointestinal cancers, gall bladder cancer, gall carcinomas, uterine cancer, cervical cancer, glioblastomas, gynecological cancers, tumors of ear, nose and throat, hematological neoplasias, hairy cell leukemia, urethral cancer, skin cancer, brain tumors (gliomas), brain metastases, testicular cancer, hypophysis tumor, carcinoids, Kaposi's sarcoma, laryngeal cancer, germ cell tumor, bone cancer, colorectal carcinoma, head and neck tumors (tumors situated in the region of the neck, nose and ears), colon carcinoma, craniopharyngiomas, cancer in the area of the mouth and on the lip, liver cancer, liver metastases, leukemia, tumor of the eyelid, lung cancer, malignant lymphoma (Hodgkin/Non-Hodgkin), lymphomas, stomach cancer, malignant melanoma, malignant neoplasma, malignomas of the gastrointestinal tract, breast carcinoma, rectum cancer, medulloblastomas, melanoma, meningiomas, Hodgkin's disease, mycosis fungoides, nose cancer, neurinoma, neuroblastoma, kidney cancer, renal cell carcinoma, Non-Hodgkin's lymphomas, oligodendroglioma, esophageal carcinoma, osteolytic tumors and osteoblastic tumors, osteosarcoma, ovarian carcinoma, pancreatic carcinoma, penile carcinoma, plasmacytoma, squamous cell carcinoma of the head and the neck, prostate carcinoma, throat cancer, rectal carcinoma, retinoblastoma, vaginal cancer, thyroid carcinoma, Schneeberg lung cancer, esophageal cancer, spinocellular carcinoma, T-cell lymphoma (Mycosis fungoides), thymoma, tube carcinoma, eye tumors, urological tumors, urothelial carcinoma, vulvar carcinoma, wart appearance, soft tissue tumors, soft tissue sarcoma, Wilm's tumor and tongue cancer.

Solid tumors are particularly preferred. Furthermore, prostate carcinomas, brain tumors, sarcomas, cervical carcinomas, ovarian carcinomas, breast carcinomas, bronchial carcinomas, melanomas, head and neck tumors, esophageal carcinomas, rectal carcinomas, pancreatic carcinomas, bladder carcinomas and kidney carcinomas, metastases in the liver, the brain and in lymph nodes are preferred.

Furthermore, the application and the use of the inventive nanoparticles together with conventional hyperthermia, radiotherapy and/or together with conventional chemotherapy are particularly preferred.

EXAMPLES

Example 1

Preparation of Nanoparticles with Coupled Mitomycin for Release

For coupling the cytostatic mitomycin to iron oxide nanoparticles stabilized by aminosilane, a conjugate of mitomycin and triethoxysilylbutyraldehyde is synthesized. For this purpose, mitomycin and triethoxysilylbutyraldehyde are dissolved in a molar ratio of 1:1 and stirred for 2 hours. In so doing, the active ingredient is coupled to the silane by means of an imine bond. Subsequently, said conjugate is used for coating iron oxide nanoparticles as follows: A suspension of non coated iron oxide particles (prepared from iron (II) chloride and iron (III) chloride by precipitation with sodium hydroxide) is set to a pH of 5 using acetic acid. Subsequently, a mixture of the mitomycin/silane conjugate and aminopropyltriethoxysilane is added under continuous stirring. The molar ratio of mitomycin to aminopropyltriethoxysilane is previously set to 1:50. After 24 hours, ethylene glycol is added so that the volume of the suspension is doubled. The water is then removed by distillation. Thus, the silanes are fixedly coupled to the iron oxide particles. The suspension is purified by dialysis against ultrapure water and concentrated to an iron concentration of 1 mol/l (by distillation).

Example 2

Coupling of an Amino Modified Oligonucleotide to Iron Oxide Nanoparticles Using Glutaraldehyde as a Linker Nanoparticles stabilized by aminosilane are prepared by precipitation of iron (II) chloride and iron (III) chloride with sodium hydroxide and coated by addition of aminopropyltriethoxysilane (according to WO 97/38058). The suspension is concentrated to an iron concentration of 2 mol/l.

500 µl of the suspension are washed with 10 ml of PIPES buffer (piperazine-N,N'-bis-2-ethane sulfonic acid; pH=7.4). Subsequently, 5% glutaraldehyde solution (6 ml) is added and the mixture is stirred for 2 hours. The particles activated thereby are washed and resuspended in 800 µl of PIPES buffer. 0.3 µmol of the amino modified oligonucleotide (amino terminal modification) are dissolved in water and added thereto. The suspension is stirred for 12 hours. Subsequently, the particles are washed with ultrapure water and resuspended in 500 µl of ultrapure water.

Example 3

Application of a Biodegradable Layer

The nanoparticles having glutaric dialdehyde linkers and oligonucleotides immobilized thereto which were prepared according to example 2 are lyophilized and treated with an ethanolic solution containing polyglycol using a spraying method. Once the solvent has been removed, nanoparticles provided with a biodegradable polyglycol coating are obtained. For example, such coatings serve for attaching aptamers and tumor cell specific antibodies.

Example 4

Coupling of Active Substances Via Oligonucleotides

Nowadays, oligonucleotide synthesis is mostly automatised and is carried out using established protective group chemistry. A short oligonucleotide consisting of 15 nucleotides is covalently coupled to the nanoparticles (see example 2). A second oligonucleotide which is complementary to the first oligonucleotide is coupled with the active ingredient doxorubicin via a terminal modification. Both components are brought together and are heated briefly to a temperature of 95° C. in order to denature the oligonucleotides. The two strands pair with each other to form a double strand due to subsequent incubation at a temperature shortly below the melting point of the oligonucleotide. The sequence of the oligonucleotide is selected such that the melting point under physiological conditions is about 48° C., thus melting of the double strand is not possible. Due to heating to more than 50° C., the DNA double strand prepared is quantitatively melted and the active ingredient is released together with the attached oligonucleotide. The single stranded DNA is quickly degraded as soon as it enters a cell, so that the active ingredient is completely released.

Example 5

Coupling of Active Substances Via Nucleic Acid Triple Helices

Double stranded RNA may be used in therapy as so called siRNA (small interfering RNA) to deactivate specific genes. In the event that such RNA is to be released under external control from the nanoparticle used as a transporter, the method of choice consists in a bond via a specific triple helix.

An oligonucleotide binding double strands and matching the siRNA used is covalently bound to the nanoparticles via a terminal modification (according to example 2). (This allows for the later formation of a so called "triplet forming oligonucleotide" (TFO)). In order to achieve an increased stability with respect to hydrolytic enzymes, such oligonucleotides are used that have the sugar phosphate backbone of the nucleic acids substituted with a synthetic peptide-like backbone which have an analogous structure to that of the nucleic acids, so called peptide nucleic acids (PNAs). The covalently bound oligonucleotide will bind the double stranded RNA in the wide groove by hybridization shortly underneath the melting point of the desired triple helix (which simultaneously is lower than the melting point of the double stranded RNA).

No significant release takes place under physiological conditions as the melting point of 45° C., in this case, is not achieved. Only by therapeutically exceeding said melting point of the triple helix, said triple helix melts while releasing the double stranded siRNA.

Example 6

Coupling of Active Substances Via an Oligopeptide Molecule

The temperature sensitive coupling via a temperature sensitive oligopeptide domain is particularly suitable for targeting genetically produced polypeptide effectors such as the tumor necrosis factor (TNFalpha). In this context, a heterodimerizing, so called leucine zipper is used. By the ionic interactions of charged groups (arginine/lysine versus glutamate/aspartate) the bond is stabilized and simultaneously specified.

At the nanoparticles, a synthetic oligopeptide consisting of 22 amino acids of the max leucine zipper is bound via a terminal modification of the oligopeptide. When a genetically produced TNF preparation terminally carrying the corresponding 22 amino acids of the myc leucine zipper is added, the tumor necrosis factor is quantitatively bound to the nanoparticles. During a thermotherapy, the melting temperature of the leucine zipper is exceeded and consequently the tumor necrosis factor (the function of which is not affected) is locally released.

Example 7

Coupling of Active Substances Via Oligonucleotide Peptide Bonds

In addition to the specific thermolabile interactions of nucleic acids with nucleic acids and of proteins with proteins (or respectively polypeptides with polypeptides) there are also specific (as well as unspecific) biological interactions between proteins or respectively polypeptides and nucleic acids. Since such interactions are based on the same non-covalent bonds, they are generally just as thermolabile as the ones mentioned before and thus they can equally be used as a thermolabile linker system for thermal release of active ingredients. Proteins are used that either interact unspecifically (e.g. histones or the single stranded SSB protein of the DNA replication fork) or highly specifically with nucleic acids (e.g. repressors, transcription factors). The so called "helix turn helix" motifs of repressor proteins as well as the so called "zinc finger" motifs of the nuclear receptor proteins are used as specific DNA binding polypeptides. Both of them typically comprise around 60 amino acids. (Zinc finger motifs consist of two equally sized loops, respectively having two pairs of cysteines, or respectively one pair of cysteines and one pair of histidines held together by a complexed zinc atom). Thus, two finger-like structures are formed, reaching into the major grooves of DNA. A linker containing an amino acid sequence which specifically recognizes a palindromic DNA sequence in the case of steroid hormone receptors and comprises between 15 and 20 amino acids is situated between the two structures.

A synthetic oligopeptide consisting of 60 amino acids and comprising the complete zinc finger motif of the glucocorticoid receptor is covalently coupled to the surface of the nanoparticles. The active ingredient molecule doxorubicin is covalently coupled to a double stranded oligonucleotide measuring 15 base pairs comprising the recognition sequence of the glucocorticoid receptor (the so called "glucocorticoid response element" GRE). Both components are coupled to form a complex which is stable under physiological conditions. If the nanoparticles are heated by the application of an alternating magnetic field, the melting temperature of the complex is exceeded. Due to the disintegration of the complex the oligonucleotide/active ingredient conjugate is released.

Example 8

Coupling of Active Ingredients Via Haptene Antibody Bonds

The spontaneous binding of a haptene as therapeutic to autologous proteins can lead to an immune reaction. The attachment of antibodies may also lead to a neutralization of the effect. Said effect is used for realizing a local activation by a thermal disintegration of haptene/antibody complexes.

So called Fv fragments (the smallest possible antigene-binding antibody fragments) of an antibody directed against doxorubicin which were produced biochemically (or optionally genetically), are covalently bound to the surface of nanoparticles. The antigene binding sites are saturated by the addition of an excess of doxorubicin. The doxorubicin saturated nanoparticles are cleared from unspecifically bound active ingredient by magnetic separation or centrifugation and, if necessary, they are additionally washed.

After intravenous administration of the doxorubicin saturated nanoparticles, said nanoparticles circulate and to a large extent they are free of the usual side effects of the cytostatic. An unspecific accumulation of the nanoparticles within the range of tumors is achieved because of the nanoparticles being able to leave the vessels through the continuously regenerated, permeable vessel walls. Additionally, the intracellular integration in tumor cells (due to mitosis frequency), but not into benign cells, can be achieved by a special surface coating. After a decent period of intratumoral accumulation, the nanoparticles can be heated by external magnetic fields; this results both in tissue damage due to hyperthermia and in the melting of the haptene/antibody (fragment) complex due to the development of heat. The tissue damaging effect of hyperthermia is potentiated due to the autonomous cytotoxic effect as well as due to the sensitizing effect with respect to radiation provoked by doxorubicins. Thus, a real synergy in tumor treatment is achieved.

Example 9

Coupling of Active Ingredients Via Biotin/Avidin Bonds

The non covalent bond between the vitamin biotin and the binding protein avidin from hen egg albumen (or respectively its bacterial analogue streptavidin) is the strongest non-covalent interaction known. Due to the high binding energy, however, the bond can not be melted within the temperature interval at disposal. For being able to still take advantage of said highly specific bond, derivatives of biotin with reduced binding strength have to be used, such as desthiobiotin (with a dissociation constant of $5 \times 10^{13}$ compared to $1 \times 10^{15}$ in the case of biotin) or iminobiotin (dissociation constant of $3.5 \times 10^{11}$), the binding of which to (strept)avidin is physiologically melted at temperatures which can be therapeutically achieved.

Iminobiotin is coupled via its ε-amino group with the amino group of doxorubicin; the bond is formed via glutaric dialdehyde. The nanoparticles are also coupled to commercially available streptavidin via an amino functionality of the surface coating by means of glutaric dialdehyde. By the addition of an excess of iminobiotinyl doxorubicin, the nanoparticles are loaded with doxorubicin. Frequently, said nanoparticles loaded with doxorubicin are passively enriched in vivo due to the permeability of the endothelial cells in the area of the tumor and additionally they are actively enriched by endocytosis in the tumor cells. In this case too, magnetically induced hyperthermia is synergetically enhanced by the thermal release of the sensitizer doxorubicin.

Example 10

Preparation of Nanoparticles with Coupled Cisplatin for Release

For coupling the cytostatic cisplatin to iron oxide nanoparticles stabilized by aminosilane, firstly, the nanoparticles characterized in example 1 are derivatized by means of aminopropyltriethoxysilane. For said purpose, a suspension of non coated iron oxide particles (prepared from iron (II) chloride and iron (III) chloride by precipitation with sodium hydroxide) is set to a pH of 5 using acetic acid. Aminopropyltriethoxysilane is added dropwise in the molar ratio with respect to the theoretical maximal number of hydroxy groups, stirred for one hour at room temperature and subsequently mixed with an equimolar amount of cisplatin which reacts in a nucleophilic substitution reaction with the amino group of the silane.

The derivatized nanoparticles obtained have the following structure:

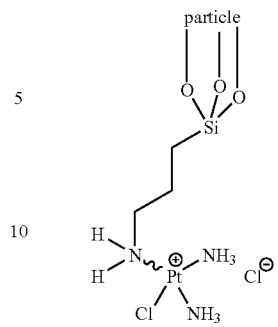

Example 11

Effect of Cisplatin Nanoparticles According to Example 10 on Glioblastoma Cells

An aqueous solution of said cisplatin nanoparticles compared to non derivatized nanoparticles in glioblastoma cells was examined.

The in vitro tests were performed with the glioblastoma human cell line RUSIRS1 (brain tumor). The glioblastoma cells were taken from tumor tissue of a patient and cultivated as described in DE 199 12 798 C1. For testing the efficiency of the cisplatin nanoparticles respectively $2 \times 10^6$ RUSIRS1 cells were prepared in a 75 cm³ cell culture bottle with 25 ml of cell culture medium (D-MEM+20% FBS+1.2 ml of pyruvate). The cell suspension was uniformly distributed on 4 culture vessels. Respectively 153 µl of aqueous solution of said cisplatin nanoparticles ($c_{Fe}$=2 mol/l) were added to two of said cell suspension. The other two culture bottles served as reference and 153 µl of aqueous solution of non derivatized nanoparticles ($c_{Fe}$=2 mol/l) were added thereto. Prior to the addition to the cells, the samples of the nanoparticles were heated to a temperature of 37° C. for 15 minutes and left at RT for 10 minutes. After the addition of the nanoparticles the samples were left for 1 hr and subsequently subjected to a treatment by an alternating magnetic field for 30 minutes. Said treatment was repeated after 24 hours. Already after an incubation time of 48 hours at 37° C., more distinct damages could be observed in the two samples with cisplatin nanoparticles than in the two samples containing non derivatized nanoparticles.

The invention claimed is:

1. A nanoparticle composition, comprising a nanoparticle, at least one linker bound to the nanoparticle, and at least one therapeutically active substance bound to the nanoparticle via the linker,
    wherein the linker is composed of nucleic acids and wherein the linker is thermolabile and is adapted to be melted upon heating of the nanoparticle composition by an alternating magnetic field, wherein the melting occurs in the range of 40° C. to 60° C. which causes, initiates, or substantially enhances separation of the at least one therapeutically active substance from the nanoparticle.

2. The nanoparticle composition according to claim 1, wherein the linker is a double stranded nucleic acid construct, a double helix, a homo hybrid or a hetero hybrid from DNA-DNA, DNA-RNA, DNA-PNA, RNA-RNA, RNA-PNA or PNA-PNA.

3. The nanoparticle composition according to claim 1, wherein at least part of the nanoparticle is coated by a protective sheath or a coating.

4. The nanoparticle composition according to claim 3, wherein the protective sheath or coating comprises amino groups or carboxyl groups.

5. The nanoparticle composition according to claim 1, wherein the at least one therapeutically active substance is selected from the group comprising antiproliferative, antimigration, antiangiogenic, antithrombotic, anti-inflammatory, antiphlogistic, cytostatic, cytotoxic, anticoagulative, antibacterial, antiviral and/or antimycotic agents.

6. The nanoparticle composition according to claim 5, wherein the at least one therapeutically active substance is selected from the group comprising actinomycin D, ametantrone, 9-Aminocamptothecin, aminoglutethimide, amsacrine, anastrozole, antagonists of purine and pyrimidine bases, anthracycline, aromatase inhibitors, asparaginase, antiestrogens, bendamustine, bexarotene, biolimus A9, bleomycin, buserelin, busulfan, calicheamicins, camptothecin, camptothecin derivatives, capecitabine, carboplatin, carmustine, chlorambucil, cisplatin, cladribine, cyclophosphamide, cytarabine, cytosine arabinoside, alkylating cytostatics, dacarbazine, dactinomycin, daunorubicin, 5'-deoxy-5-fluorouridine, docetaxel, doxorubicin (adriamycin), doxorubicin lipo, epirubicin, estramustine, etoposide, exemestane, fludarabine, fluorouracil, folic acid antagonists, formestane, gemcitabine, glucocorticoids, goserelin, hormones and hormone antagonists, hycamtin, hydroxyurea, idarubicin, ifosfamide, imatinib, irinotecan, letrozole, leuprorelin, lomustine, maytansinoids, melphalan, mercaptopurine, methotrexate, miltefosine, mitomycins, mitopodozide, antimitotic agents, mitoxantrone, nimustine, oxaliplatin, oxazaphosphorines, paclitaxel, pentostatin, podophyllotoxin derivatives, procarbazine, rapamycin, rhodomycin D, tamoxifen, temozolomide, teniposide, testolactone, thiotepa, thioguanine, topoisomerase inhibitors, topotecan, treosulfan, tretinoin, triptorelin, trofosfamides, vinca alkaloids, vinblastine, vincristine, vindesine, vinorelbine, cytostatically active antibiotics.

7. The nanoparticle composition according to claim 5, wherein the at least one therapeutically active substance is selected from the group comprising nucleic acids, amino acids, peptides, proteins, carbohydrates, lipids, glycoproteins, glycans or lipoproteins, wherein the aforementioned substances have antiproliferative, anti-migration, antiangiogenic, antithrombotic, anti-inflammatory, antiphlogistic, cytostatic, cytotoxic, anticoagulative, antibacterial, antiviral and/or antimycotic properties.

8. The nanoparticle composition according to claim 1, wherein the nanoparticle comprises superparamagnetic iron oxides or pure iron having an oxide layer.

9. The nanoparticle composition according to claim 1, further comprising a sensitizer, radiosensitizer and/or amplifier bound to the nanoparticle for complementing conventional cancer treatment methods.

10. The nanoparticle composition according to claim 1, further comprising monoclonal antibodies or respectively antibody fragments and/or aptamers bound to the nanoparticle for conveying target finding properties to the nanoparticle composition.

11. A pharmaceutical composition comprising the nanoparticle composition of claim 1 and a pharmaceutically acceptable carrier, wherein the pharmaceutical composition is adapted for infusion or injection.

12. A method comprising administering the pharmaceutical composition of claim 11 to a mammal for the treatment of proliferative diseases, cancer and bacterial infections, wherein the administering is an administration to a tumor or infection site, followed by application of an alternating magnetic field.

13. A nanoparticle composition of claim 1, wherein the nanoparticle is adapted to be heated by an alternating magnetic field.

14. A nanoparticle composition of claim 1, wherein the separation of the at least one therapeutically active substance from the nanoparticle occurs at a temperature of more than 45° C.

15. The nanoparticle composition of claim 1, wherein the linker is composed of oligonucleotides.

16. The nanoparticle composition of claim 1, wherein the therapeutically active substance is siRNA.

17. A nanoparticle composition, comprising a nanoparticle, at least one linker bound to the nanoparticle, and at least one therapeutically active substance bound to the nanoparticle via the linker,
wherein the linker is composed of polypeptides, and wherein the linker is thermolabile and is adapted to be melted upon heating of the nanoparticle composition by an alternating magnetic field, wherein the melting occurs in the range of 40° C. to 60° C. which causes, initiates, or substantially enhances separation of the at least one therapeutically active substance from the nanoparticle.

18. The nanoparticle composition of claim 17, wherein the linker is composed of polypeptides which form homo dimers or hetero dimers.

19. A nanoparticle composition, comprising a nanoparticle, at least one linker bound to the nanoparticle, and at least one therapeutically active substance bound to the nanoparticle via the linker,
wherein the linker is composed of nucleic acids or polypeptides, and wherein the linker is thermolabile and is adapted to be melted upon heating of the nanoparticle composition by an alternating magnetic field, wherein the melting occurs in the range of 40° C. to 60° C. which causes, initiates, or substantially enhances separation of the at least one therapeutically active substance from the nanoparticle.

20. A method comprising administering the pharmaceutical composition of claim 11 to a mammal for the treatment of cancer, wherein the administering is an intratumoral administration.

* * * * *